(12) United States Patent
Shapiro

(10) Patent No.: US 8,067,183 B2
(45) Date of Patent: Nov. 29, 2011

(54) METHODS AND COMPOSITIONS FOR DEVELOPMENT OF DRUG SCREENING PROCEDURES AND DIAGNOSTIC TOOLS

(76) Inventor: Howard K. Shapiro, Narberth, PA (US)

( * ) Notice: Subject to any disclaimer, the term of this patent is extended or adjusted under 35 U.S.C. 154(b) by 814 days.

(21) Appl. No.: 11/827,425

(22) Filed: Jul. 12, 2007

(65) Prior Publication Data

US 2007/0269834 A1    Nov. 22, 2007

Related U.S. Application Data

(63) Continuation-in-part of application No. 09/194,619, filed on Aug. 25, 2003, now abandoned.

(51) Int. Cl.
*G01N 33/53* (2006.01)
(52) U.S. Cl. ........................................ 435/7.1
(58) Field of Classification Search .................. None
See application file for complete search history.

(56) References Cited

U.S. PATENT DOCUMENTS 4,012,288 A * 3/1977 Lyman et al. .............. 435/305.2

FOREIGN PATENT DOCUMENTS

WO    95/05466 *    2/1995

OTHER PUBLICATIONS

Sigma Cell Culture catalog 1994 edition, p. 143.*
Malow 1989 (Arch Neurol 46:1201-1203).*
Tesco 1992 (Mechanisms of Ageing and Development 66:117-120).*
Vile 1995 (Free Radical Biology & Medicine 18(4):721-730.*
Dreher 1995 (Electrophoresis 16(7):1205-1214).*
Edwards 1991 (Journal of Investigative Dermatology 96:392-396).*

* cited by examiner

*Primary Examiner* — Daniel E Kolker

(57) ABSTRACT

This invention defines novel research methodology for use in (a) monitoring the ongoing status of the physiological expression of Charcot-Marie-Tooth disease and (b) screening candidate therapeutic drug agents for possible effectiveness. The presence of this neurodegenerative disease can be characterized in part by the expression in cultured fibroblasts obtained from the patient of one or more proteins which are not the product of a defective disease-inducing gene, but which are stress proteins, one or more other proteins modified by conditions of oxidative stress or other disease-related proteins. This candidate drug screening technology offers advantages in terms of (a) providing new research opportunities, (b) cost effectiveness, (c) ability to be used readily on a large scale, (d) ability to generate meaningful data in a comparatively short period of time, and (e) providing an opportunity to obtain information based on direct interaction of a candidate drug and a living tissue disease model.

19 Claims, No Drawings

//METHODS AND COMPOSITIONS FOR DEVELOPMENT OF DRUG SCREENING PROCEDURES AND DIAGNOSTIC TOOLS

RELATED PATENT APPLICATION

This invention is a continuation-in-part of U.S. patent application Ser. No. 09/194,619, filed on Aug. 25, 2003, entitled "Methods and Compositions for Development of Drug Screening Procedures and Diagnostic Tools," now abandoned, the disclosure of which is incorporated by reference herein.

BACKGROUND OF THE INVENTION

1. Field of the Invention

The present invention relates to new diagnostic procedures or to protocols suitable for use in screening candidate therapeutic drug agents. The present invention provides human, living, dynamic experimental models, and metabolic markers related thereto, for examining some aspects of the pathophysiology of familial or non-familial neuro-degenerative diseases selected from the group hereby limited solely to Charcot-Marie-Tooth disease, familial Alzheimer's disease, familial Parkinson's disease, Huntington's disease, spinal muscular atrophy, Friedreich'a ataxia, giant axon neuropathy, juvenile ceroid-lipofuscinosis, familial motor neuron diseases, juvenile diabetic polyneuropathy and Down's syndrome, including various individual genetic subvarieties thereof.

2. Description of Prior Art

J. T. Coyle and P. Puttfarcken (1993), *Science* 262:689-695 (1993) noted that

There is an increasing amount of experimental evidence that oxidative stress is a causal, or at least an ancillary, factor in the neuropathology of several adult neurodegenerative disorders, as well as in stroke, trauma, and seizures . . . [pg. 689]

The authors proceeded to review the various sources and origins of neuronal oxidative stress and reviewed the known intrinsic metabolic mechanisms for natural protection against such stress. They mentioned the ability of vitamin E to inhibit lipid peroxidation (pg. 690, first column, lines 5-9), and they referred to the neuroprotective effect of other antioxidants (i.e., page 692, column one). Notably, on page 690, second column, lines 1-5 the authors also mentioned that Furthermore, peroxy radicals can combine with an abstracted hydrogen atom to form lipid hydroperoxides which, in the presence of $Fe^{2+}$, decompose to alkoxy radicals and aldehydes.

On page 692 (column three, lines 7-11) the authors specifically mentioned that they were referring to diseases such as Parkinson's disease (PD), amyotrophic lateral sclerosis (ALS) and Huntington's disease (HD). In another statement of particular relevance (page 693, column three, lines 32-39), the authors commented that . . . notably, protein carbonyl content, a measure of protein oxidation, was elevated by 85% in patents with sporadic ALS as compared to controls, suggesting that oxidative stress is a common feature of ALS whether the disease is due to loss of CuZnSOD activity or to other causes . . .

The authors concluded (page 694, column two, lines 5-11), in part

. . . Nevertheless, the evidence, while still largely circumstantial, is convincing that oxidative stress represents an important pathway, initiated in part by Glu, that leads to neuronal degeneration in a manner consistent with the course and pathology of several degenerative disorders of the brain . . .

One aspect of cellular oxidative stress is the pathological formation of crosslinked proteins. As the H polypeptide chains of neurofilaments have an especially high lysine content (20%), neurofilaments are particularly susceptable to spurious crosslinking reactions which may be induced by lipid peroxidation products [Carden et al., *Neurochem. Pathol.* 5:25-35 (1986)]. The results of several published research studies suggest that dysfunctional lipid peroxidation may be a contributing factor in the etiology of Parkinson's disease [Fahn, *Ann. NY Acad. Sci.* 570:186-196 (1989)], multiple sclerosis [Hunter et al., *Neurochem. Res.* 10:1645-1652 (1985)] and Duchenne muscular dystrophy [Kar and Pearson, *Clin. Chim. Acta* 94:277-280 (1979); Jackson et al., *Med. Biol.* 62:135-138 (1984); Hunter and Mohamed, *Clin. Chim. Acta* 155:123-132 (1986)].

A considerable body of prior art has provided evidence suggesting that the etiologies of certain neurodegenerative diseases include evidence of chemical crosslinking of neurofilaments. Such studies include work on Charcot-Marie-Tooth (CMT) genetic neuropathies [Hughes and Brownell, *J. Neurol. Neurosurg. Psych.* 35:648-657 (1972); Brimijoin et al., *Science* 180:1295-1297 (1973); van Weerden et al., *Muscle & Nerve* 5:185-196 1982; and Goebel et al., *Ital. J. Neurol. Sci.* 7:325-332 1986)], giant axon neuropathy [Prineas et al., *J. Neuropathol. Exp. Neurol.* 35:458-470 (1976)], diabetic polyneuropathy [Yamamura et al., in *Diabetic Neuropathy*, Goto, Y, sr, ed. (Princeton, Excerpta Medica, (1982) pp. 80-85; Sidenius and Jakobsen, *Diabetes* 31:689-693 (1982); and Tomlinson and Mayer, *J. Auton. Pharmac.* 4:59-72 (1984)], Alzheimer's disease [Wisniewski et al., *J. Neuropath. Exp. Neurol.* 29:163-176 (1970); and Wisniewski et al, in *Aging and Cell Structure*, volume 1, Johnson, Jr., J E, ed. (New York, Plenum Press, 1982) pp. 110-112], Down's syndrome [Goodison et al., *Soc. Neurosci. Abstr.* 15(pt. 2): 329 (abstract 135.6) (1989)], Pick's disease [Yoshimura, *Clin. Neuropath.* 8:1-6 (1989)], Parkinson's disease [Oppenheimer, in *Greenfield's Neuropathology*, Blackwood, W and Corsellis, JAN, eds. (Chicago, Year Book Medical Publishers, 1976) pp. 612-614; and Cohan, in *Clinical Aspects of Aging*, third edition, Reichel, W, ed. (Baltimore, Williams & Wilkens, 1989) pp. 167)], amyotrophic lateral sclerosis [Carpenter, *Neurology* 18:841-851 (1968)], infantile spinal muscular atrophy [Lee et al., *Neuropediatrics* 20:107-111 (1989)], Friedreich's ataxia [Lamarche et al., *Can. J. Neurol. Sci.* 9:137-139 (1982)], and alcoholic polyneuropathy [Appenzeller and Richardson, *Neurology* (Minneap) 16:1205-1209 (1966)].

Considerable biomedical literature indicates that certain sites on normal proteins and lipids are specific targets for spurious chemical crosslinking, most notably the ε-amino groups of lysine residues in proteins and the amine groups of phosphatidyl-ethanolamine molecules in cell lipid membrane bilayers. These primary amine groups are especially prone to attack by small molecular weight carbonyl-containing hydrocarbons. Such carbonyl-containing molecules may originate by many pathological mechanisms still only partly defined, but, in general, they originate from peroxidation of fatty acids or as by-products of sugar metabolism. A mono-carbonyl specie can bind to a protein or amino-lipid, alter its three dimensional structure and possibly affect its chemical activity. A dicarbonyl hydrocarbon can react with two amine groups, thus making a covalent chemical crosslink. The specific primary pathological changes that underlie this type of deterioration remain largely undefined, but their structural products have been characterized in many respects.

For example, the senile plaques and neurofibrillary tangles typical of Alzheimer's disease consist largely of networks of intermediate size protein filaments helically wound in pairs having a periodicity of 80 nm [Selkoe et al. *Science* 215:1243-1245 (1982)]. Isolated paired helical filament (PHF) has proven to have remarkable properties of chemical stability. PHF chemical crosslinking bonds are not broken by sodium dodecyl sulfate, β-mercaptoethanol, 9.5 M urea, two percent Triton X-100, one percent NP-40, 6 M guanidine hydrochloride, 0.2 N HCl or 0.2 N NaOH. As heating of PHF in the presence of either reducing agents such as β-mercaptoethanol or detergents such as Triton X-100 or NP-40 did not solubilize PHF, bonds other than disulfide are implicated in amino acid crosslinking of this type of rigid intracellular polymer. This unusual chemical stability has seriously impeded PHF analysis by gel electrophoresis [Selkoe et al. (1982)]. As a postulated mechanism for such unusual crosslinking Selkoe et al. noted that "different protein polymers in senile cataracts, terminally differentiated epidermal cells, and red blood cells are covalently cross-linked by γ-glutamyl-ε-lysine sidechain bridges." Like PHF, these other protein complexes are insoluble in sodium dodecyl sulfate and not solubilized by reducing agents. Selkoe et al. speculated that such γ-glutamyl-ε-lysine crosslinks may also form pathologically in nerve cells, as human brain contains a transglutaminase capable of acting on normal neurofilament to form an insoluble high molecular weight filamentous polymer.

Kikugawa and Beppu [*Chem. Phys. Lipids* 44:277-296 (1987)] noted that lipid radicals, hydroperoxides and their secondary products (including various aldehydes and ketones) react with neighboring protein molecules, damaging protein structure and function. Such damage includes formation of fluorescent chromophores, lipid-protein adducts, and protein-protein crosslinks. Using sodium dodecyl sulfate-polyacryl-amide gel electrophoresis, these investigators demonstrated that malonaldehyde (also known as malondialdehyde), a bifunctional molecule having two aldehyde groups, can covalently crosslink proteins. This reaction primarily involves Schiff base formation with protein ε-amino groups on the sidechains of lysine residues. Kikugawa and Beppu (1987) also reported that monofunctional aldehydes such as acetaldehyde, 1-hexanal, 1-heptanal and 2,4-decadienal can also crosslink proteins, generating fluorescent products. This biochemical curiosity still not well understood. Some form of self-condensation may be involved.

A report by Piersanti et al. [*Neurobiol. Aging* 13:S111 (abstract 437) (1992)] documented an increased susceptibility of Alzheimer's disease patient skin fibroblasts to free radical damage. The Piersanti report, taken together with CMT research findings discussed below, lends credence to the concept that skin fibroblast samples from patients having other neurodegenerative disorders will also show evidence of oxidative stress.

Evidence of increased deposition of lipofuscin in various neurodegenerative diseases has been presented. This observation has been documented in studies on amyotrophic lateral sclerosis [Carpenter (1968)], Guam Parkinsonism-dementia [Tan et al., *Clin. Exp. Neurol.* 17:227-234 (1981)], Alzheimer's disease [Tsuchida et al., *Chem. Phys. Lipids* 44:297-325 (1987); Moran and Gomez-Ramos, *Soc. Neurosci. Abstr.* 15(pt. 2):1039 (abstract 414.8) (1989)], Huntington's disease [Tellez-Nagel et al., *J. Neuropathol. Exp. Neurol.* 33:308-332 (1974)], Meniere's disease [Ylikoski et al. *Arch. Otolaryngol.* 106:477-483 (1980)], and juvenile ceroid-lipofuscinosis [Schwendemann, in *Ceroid-Lipofuscinosis (Batten Disease)*, Armstrong, D, sr. ed. (New York, Elsevier Biomedical Press, 1982) pp. 117-136]. Heart lipofuscin has been shown to have the following general composition: lipids, 20-50%; protein, 30-60%; and strongly pigmented resin-like hydrolysis-resistant material, 9-20%. Although the exact nature of the hydrolysis-resistant chemical bonds remains to be unequivically defined, the similarity between lipofuscin fluorescence and that of Schiff bases formed between malonaldehyde and primary amines suggests that similar chemical crosslinks may be part of lipofuscin structure [Tsuchida et al. (1987)].

Another fundamental physiological aspect of metabolic oxidative stress is the induction of genes that code for stress proteins, originally known as heat shock proteins (hsp's). Highly conserved genes for these proteins are present in bacteria, plants, yeast and higher animals [Welch, *Sci. Am.* 268(5):56-64 (1993, pgs. 61-62)]. A wide variety of environmental stimuli are known to induce the expression of these genes, including brief exposures to elevated temperatures, exposure to toxic metals, alcohols, various metabolic poisons, protein denaturants and conditions which induce ischemia/reperfusion trauma (i.e., oxidant injury). Welch [*Sci. Am.* 268(5):56-64 (1993, pgs. 61-62)] noted that > In animal studies, researchers have observed the induction of stress responses in both the heart and brain after brief episodes of ischemia and reperfusion . . .
>
> Cells that produce high levels of stress proteins appear better able to survive the ischemic damage than cells that do not . . .

To some limited extent, some hsp's are normally (i.e., constitutively) expressed in plant, microbial and animal cells. They play a role in normal protein post-translational processing and normal metabolic turnover of proteins. Yet even constitutive hsp's are stress inducible. Of the several different classes of hsp's, the hsp70 gene family is the most stress-inducible member.

Heretofore, some thought has been given to the question of what role hsp's might play in the neurodegenerative diseases addressed herein. However, the question has received little previous attention, and only within a quite limited scope. Autosomal dominant familial forms of Parkinson's disease are now well recognized [Gasser et al., *Ann. Neurol.* 36(3): 387-396 (1994)]. However, a Medline database search from 1976 to April 1995 for references addressing familial Parkinson's disease and stress proteins generated no matches. When a Medline database search from 1976 to April 1995 was expanded to include non-familial cases of Parkinson's disease and stress proteins two references were found [Renkawek et al., *Acta Neuropath.* 87(5):511-519 (1994) and Namba et al. [Japanese] *No to shinkei [Brain & Nerve]* 43(1): 57-60 (1991)]. However, both of these studies were based on analysis of brain tissue and neither disclosed nor anticipated the present invention.

Likewise, numerous publications have reported genetic forms of Alzheimer's disease [Campion et al. *Neurology* 45(1):80-85 (1995)]. A Medline database search from 1976 to April 1995 for references addressing familial Alzheimer's disease and stress proteins generated only one match [Guillemette et al., *J. Neurochem.* 47(3):987-997 (1986)], but actually this paper did not mention that any of its Alzheimer patients had a genetic form of the disease. The report by Guillemette et al. described studies on RNA transcripts obtained from post-mortem Alzheimer's brain biopsy samples. They observed elevated levels of hsp mRNA transcripts in brain samples from Alzheimer patients who had fever immediately prior to death. They also studied human brain mRNA translation (i.e., protein) products. Guillemette et al. reported, in part, that A positive correlation was found between elevated amounts of the 70-kDa protein and an agonal process accompanied by fever. Two-dimensional analysis of the protein products showed two or more polypeptides for each 70-kDa protein band observed in one-dimensional gels . . . The protein patterns resemble those reported for heat-treated HeLa cells (Slater et al., 1981), suggesting the possibility that heat-shock proteins are expressed in human brain during agonal processes accompanied by fever . . . Despite similarities in the fever profile during the agonal process, control (FIGS. 4b and e) and [Huntington's disease] non-Alzheimer dementia-associated brains (FIGS. 4c and f) exhibited higher yields of 70-kDa peptides than those from Alzheimer-afflicted brains . . .

. . . These results indicate that Alzheimer's disease, in the absence of fever, is not associated with heat-shock response. [pg. 993]

. . . To examine the possibility that the primary pathogenic events that initiate Alzheimer's disease may induce heat-shock expression in the absence of fever, we probed total RNA from the neocortex of an otherwise healthy patient with Alzheimer's disease who died quickly from suicide by hypoxia (K513, FIG. 5, lane 3). There was no detectable expression of the [hsp70] heat-shock transcript in this case . . . [pgs. 994-995].

Hence, Guillemette et al. restricted their study to analysis of brain samples and did not consider the possibility that stress proteins might be expressed preferentially in cultured non-neuronal tissue. They additionally investigated postmortem brain samples from several Huntington's disease patients, which may explain why this paper is considered to be a genetic study in the Medline database system. Yet for this familial neurodegenerative disorder also, Guillemette et al. attributed the expression of hsp70 to the presence of agonal fever (pg. 993). These investigators did not consider Huntington's disease fibroblasts in their studies. Hence, the present invention was not anticipated by Guillemette et al.

A Medline database search from 1976 to April 1995 was expanded to include references addressing non-familial Alzheimer's disease and stress proteins, and several additional reports were found. Yet none disclosed or anticipated the present invention. A representative sampling of these is presented below. The findings of Guillemette and coworkers regarding hsp expression in Alzheimer's disease postmortem brain samples have been independently confirmed by Morrison-Bogorad et al. [*J. Neurochem.* 64(1): 235-246 (1995)], who noted that . . . approximately 40% of the [Alzheimer's disease] patients had a recorded fever of > or =39.2 degrees at or near death . . . Levels of hsp70 mRNAs were increased three- to 33-fold in cerebellum of febrile patients compared with levels in patients whose recorded temperatures were < or =37.5 degrees C. . . . These results indicate that a specific agonal stress, namely fever, can increase the levels of heat shock 70 mRNAs in AD brain . . .

Renkawek and coworkers (1994) reported immunohistochemical and immunoblotting findings which indicated a "highly induced" expression of hsp27 in Alzheimer brain samples. They also noted that hsp27 expression was also induced, albeit to a lesser extent, in brain samples obtained from patients having other types of dementia, such as Parkinson's dementia, multi-infarct dementia and normal pressure hydrocephalus. Shinohara et al. [*J. Neuro. Sci.* 119(2):203-208 (1993)] reported that increased levels of two other small heat shock proteins, α-B crystallin and hsp28, were also found in Alzheimer brain samples. Using an antibody specific for α-B crystallin to immunostain nerve samples from patients having several neurodegenerative diseases, Lowe et al. [*Neuropath. Appl. Neurobiol.* 18(4):341-350 (1992)] studied ballooned neurons having excess phosphorylated neurofilaments. They found that ballooned nerve samples obtained from classical Pick's disease cases, Alzheimer's disease cases and motor neuron disease cases all showed "strong diffuse cytoplasmic immunoreactivity." They concluded that " . . . α-B crystallin may be involved in aggregation and remodelling of neurofilaments in disease."

Using cultured neuronal PC12 cells which had been heat shocked by incubation at 45° C. for 30 minutes, Johnson et al. [*Annals NY Acad. Sci.* 695:194-197 (1993)] reported evidence of induced expression of hsp72, alterations in the phosphorylation and metabolism of amyloid precursor protein (APP), and formation of a stable complex between hsp72 and tau. Johnson et al. concluded that "these results suggest that heat shock proteins may play either a protective or a promoting role in the formation of A68 and/or the amyloidogenic C-terminal fragment of APP." Speculating along similar conceptual lines, Hoyer [*J. Geriatr. Psych. Neurol.* 6(1):3-13 (1993)] stated that in the earliest stages of Alzheimer's disease several stress-related physiological abnormalities, such as glycogen accumulation, might induce the expression of hsp's, and that such events might lead to enhanced generation of amyloid precursor protein. Two other reported studies in this general field, the work of Abe et al. [*Neurosci. Letters* 125(2):169-171 (1991)] which used cultured lymphoblastoid cells and the work of Morandi et al. [*Prog. Clin. Biol. Res.* 317:819-827 (1989)] which used cultured rat dorsal root ganglial cells, failed to disclose or anticipate the invention embodied herein.

Approximately 10% of patients having amyotrophic lateral sclerosis (ALS), one of the motor neuron diseases, have a familial form of this disease [Marx, *Science* 259:1393 (1993)]. Familial cases of ALS are now known to result from a defect in the gene which codes for Cu/Zn-binding superoxide dismutase, an enzyme involved in oxidative free radical metabolism. A Medline database search from 1976 to May 1995 for citations regarding ALS and stress proteins generated three matches [i.e., Migheli et al. *Neuropathol. Appl. Neurobiol.* 20(3):282-289 (1994)]. Yet all three of these reports were based on studies of anterior horn cell neuronal tissue and none disclosed or anticipated the present invention. When an ALS/stress protein Medline database search from 1976 to May 1995 was expanded to include fibroblasts as a main heading three additional studies were listed [Witt et al., *J. Neurol. Sci.* 126(2):206-212 (1994); Tandan et al., *J. Neurol. Sci.* 79(1-2):189-203 (1987); and Beach et al., *J. Neurol. Sci.* 72(1):49-60 (1986)]. However, the Witt paper focused on calcium homeostasis in ALS fibroblasts. The Tandan et al. study focused on DNA repair abilities of ALS fibroblasts. The Beach et al. study focused on collagenase activity in ALS fibroblasts. None of these additional studies included work on stress proteins. Hence none of them disclosed or anticipated the present invention.

The appearance of high molecular weight ubiquitin-protein conjugates under stress protein inducing conditions is a well documented phenomenon [Raboy et al. *Acta Biol. Hung.* 42(1-3):3-20 (1991), pg. 8]. Ubiquitin-protein conjugates such as ubiquitinated paired helical filaments [Morishima-Kawashima et al. *Neuron* 10(6): 1151-1160 (1993)] have been described in studies based on analysis of nerve biopsy tissue. Yet a Medline review of ubiquitin prior art has not revealed a previous search for or identification of disease-associated ubiquitin-protein conjugates in fibroblasts obtained from patients having neurodegenerative diseases.

In U.S. Pat. No. 5,348,945 P. A. Berberian et al. described compositions for and methods of treating certain physiological stress-related states by use of an hsp70 protein as a medicinal agent. The invention embodied in U.S. Pat. No. 5,348,945 is beyond the scope of and irrelevant to the practice of the present specification. The methods and compositions of the present invention were neither disclosed nor anticipated by Berberian et al. Indeed, as defined below, the exogenous introduction of an hsp70 protein into any of the methods and compositions of the present invention would only serve to invalidate the findings, thus rendering useless the practice of the present invention.

DETAILED DESCRIPTION OF THE INVENTION

Drug Screening Methodology

Many previously described pathophysiological aspects of the diseases addressed herein have been of a quantiative, i.e., incremental, nature. However, the present invention is based on the monitoring of one or more qualitative metabolic markers, i.e., the appearance of stress proteins and possibly other proteins secondarily related to disease etiology in cultured fibroblasts.

None of the one or more protein metabolic markers referred to in the present invention is known to be the direct translation product of a defective gene responsible for a particular familial neurodegenerative disease. It is the understanding of the inventor that the detectable expression of secondary disease-related proteins in cultured cells, which is the basis of the present invention, may not be immediately apparent when cultured fibroblast cell strains are initially established, and that each cell strain must be followed through several culturing passages so as to determine the point at which such events first occur. As noted by Welch and Feramisco [*J. Biol. Chem.* 257(24):14949-14959 (1982), pg. 14958], the cell culture environment may be regarded as a kind the stress condition capable of inducing the expression of various stress proteins by several different cell types. As illustrated below with a form of Charcot-Marie-Tooth disease, the inventor has observed that fibroblast cells derived from human donors having a genetic neurodegenerative disease will predictably respond differently than comparable cells obtained from genetically normal donors, with the genetically defective cells showing a predisposition towards expression of stress proteins and other proteins secondarily related to disease etiology.

The results of a study conducted by the present inventor and disclosed in U.S. patent application Ser. No. 08/062,201 provide evidence that chemical crosslinking of neurofilaments may underlie at least part of the etiology of chromosome 17 Charcot-Marie-Tooth disease (type 1a CMT). Cultured skin fibroblasts from three chromosome 17 CMT donors and three control donors matched for age and sex were analyzed by two-dimensional gel electrophoresis and subsequent computer image analysis.

Cultured human fibroblast strains used in this study were obtained from the collection established by the present inventor in the laboratory of Howard Goldfine, Ph.D. of the Microbiology Department, University of Pennsylvania Medical School. For each of the six skin biopsy fibroblast strains examined, cells were grown in vitro in pH 7.4 RPMI 1640 media supplemented with 10% fetal calf serum and L-glutamine. Fibroblasts were grown to confluency and then divided 1:3 for each sub-culture. Sixth sub-culture fibroblasts were used for protein analysis by gel electrophoresis.

The protein contents of these six cultured fibroblast strains were subjected to two-dimensional gel electrophoresis according to the procedure of Carrels [*J. Biol. Chem.* 254: 7961-7977 (1979)]. Cultured fibroblast proteins were extracted into a sample buffer containing 0.3% sodium dodecyl sulfate, 5.0% β-mercaptoethanol and Tris buffer, pH 8.0. For each sample, 30 pg protein was applied to a 2.7% acrylamide gel containing 2.0% ampholytes (pH range 5-7). After isoelectric focusing electrophoresis, the proteins of each sample were resolved in the second dimension according to molecular weight on a 12.5% acrylamide gel. Protein gel spots were visualized by use of silver staining according to the methods of Merril et al. [*Proc. Nat. Acad. Sci. USA* 76:4335-4339 (1979) and *Science* 211:1437-1438 (1981)] and Morrissey [*Anal. Biochem.* 117:307-310 (1981)]. Identification of individual protein spots on each gel was accomplished by electronic image processing followed by use of the PDQUEST™ computer analysis system (Protein Databases, Inc.).

In this study 145 protein spots were always seen in each of the three normal fibroblast strains, and 126 corresponding protein spots were always seen in each of the CMT strains. There were no examples of a protein always seen in each of the control samples but never seen in any of the CMT samples. However, each of the CMT samples also showed 25 additional protein spots that were never seen in any of the control samples. The available information on these CMT-specific proteins may be summarized below as noted in Table 1.

The distribution of molecular weights of the additional CMT-specific protein spots did not correspond to the molecular weight distribution of control protein spots. Rather, it was comparatively shifted up scale. Of the protein spots always seen in control samples, the largest had a molecular weight of 118,000 Da. Of the 25 CMT-specific protein spots, nine had molecular weights in the range of 130,000 to 192,000 Da.

Such protein mapping data cannot readily be explained by simple genetic principles. The appearance of many supernumerary protein spots associated with a genetic defect might be explained by a post-translational event, such as excess protein phosphorylation. Such events, however, would be expected to have relatively small effects on observed protein molecular weights. Hence such an explanation appears to lack credence in this case. In fact, the information available from this study can most directly be interpreted as evidence of excess, pathological chemical crosslinking of fibroblast proteins. Should corresponding protein crosslinking occur into the peripheral nerves of these patients, this may be a fundamental aspect of type 1a CMT 1a disease etiology.

TABLE 1

| sample spot number (SSP) | apparent molecular weight | apparent isoelectric point (pI) |
|---|---|---|
| 1609 | 89,300 | 4.53 |
| 2120 | 33,100 | 4.95 |
| 2306 | 55,100 | 5.03 |
| 2604 | 94,200 | 5.10 |
| 2704 | 130,700 | 4.92 |
| 2705 | 130,400 | 4.97 |
| 2708 | 149,000 | 4.97 |
| 2709 | 149,000 | 5.01 |
| 2710 | 150,600 | 5.11 |
| 3305 | 53,000 | 5.35 |
| 3710 | 145,400 | 5.37 |
| 4201 | 37,000 | 5.71 |

TABLE 1-continued

| sample spot number (SSP) | apparent molecular weight | apparent isoelectric point (pI) |
|---|---|---|
| 4304 | 47,600 | 5.46 |
| 4407 | 63,700 | 5.42 |
| 4516 | 71,400 | 5.57 |
| 4519 | 73,400 | 5.48 |
| 5409 | 67,900 | 5.92 |
| 5413 | 67,700 | 5.84 |
| 5612 | 109,500 | 5.77 |
| 6106 | 29,000 | 6.42 |
| 6303 | 46,300 | 6.48 |
| 6517 | 80,300 | 6.30 |
| 6702 | 138,200 | 6.31 |
| 6704 | 159,500 | 6.25 |
| 6801 | 192,800 | 6.26 |

Reiter et al. [*Nature Genetics* 12:288-297 (1996)] have reported that in CMT patients such as those used in this study a segment of chromosome 17 has been duplicated. This segment, which lies adjacent to (i.e., in tandem with) the corresponding original segment of DNA, includes an intact copy of the gene coding for peripheral myelin protein 22 (PMP-22) as well as perhaps as many as 30 additional intact genes. However, these duplicated genes would reasonably be expected to only increase the translational expression of their corresponding protein products by approximately fifty percent. That is, mitotic cells normally contain two copies of each autosomal gene, while mitotic cells of this variety of CMT disease contain one normal chromosome 17 and one anomalous chromosome 17 that bears a duplicated segment. Hence, the relative expression of disease-specific gene products in this case should be approximately 3:2, compared to corresponding normal cells. Yet, in contrast, the supernumerary proteins reported in the present example were never detectably expressed in any of the three corresponding normal fibroblast samples. Although it was not known when the CMT protein mapping study reported above was done, it is now known that the chromosome 17 PMP-22 gene is in fact expressed in human fibroblasts [Valentijn et al. *Nature Genetics* 1:166-170 (1992); Bosse et al. *J. Neurosci. Res.* 37(4):529-537 (1994); Suter et al. *J. Biol. Chem.* 269(41):25795-25808 (1994)].

Subsequent to the present inventors original analysis of his two-dimensional gel electrophoresis study of CMT fibroblast proteins as previously disclosed in U.S. patent application Ser. No. 08/062,201, in 1995 he reviewed the prior art literature regarding the molecular weight and isoelectric focusing point data of known human stress proteins and observed direct matches between four of them and corresponding CMT-specific proteins characterized in the CMT protein mapping study. These findings may be summarized as follows:

(1) CMT-specific protein spot SSP 4516 [using nomenclature of the original 1988 Protein Databases, Inc, report] has an apparent molecular weight of 71,400 Da and a pI of 5.57. These data correspond to the 72 kDa stress protein referred to on pg. 14956 of Welch and Feramisco [*J. Biol. Chem.* 257: 14949-14959 (1982)], reported to have a pI of 5.6. This 72-kDa/pI 5.6 stress-inducible protein is also discussed by Minota et al. [*J. Exp. Med.* 168:1475-1480 (1988)].

(2) CMT-specific protein spot SSP 4519 has an apparent molecular weight of 73,400 Da and a pI of 5.48. These data correspond to the 73 kDa stress protein referred to on pg. 14956 of Welch and Feramisco (1982), reported to have a pI of 5.5. This 73-kDa/pI 5.5 stress-inducible protein is also discussed in Minota et al. (1988).

(3) CMT-specific protein spot SSP 5409 has an apparent molecular weight of 67,900 Da and a pI of 5.92. These data correspond to the 68 kDa human stress protein which has a pI of 5.9, as discussed in Ohno et al. [*J. Biol. Chem.* 263:19764-19770 (1988)].

(4) CMT-specific protein spot SSP 5413 has an apparent molecular weight of 67,700 Da and a pI of 5.84. These data correspond to the 68 kDa human stress protein which has a pI of 5.8, as discussed in Ohno et al. (1988).

Hence, all four of the stress proteins identified in CMT fibroblasts are members of the HSP 70 multigene family. Even an apparently contradictory observation in the original CMT protein mapping study now appears to make more sense in light of the observations noted above. Protein Databases additionally tested one pair of CMT and control skin biopsy explants, which basically were just minced pieces of skin. The data from these two samples did not show evidence of the characteristic CMT-specific protein spots. However, some information has appeared which suggests that in vitro tissue culture may be a form of stress protein inducing environment. This point has been previously noted by Welch & Feramisco (1982, pg. 14958):

while the 72, 80, 100 and 110 kd [stress] proteins are present in apparently low amounts, the 73 and 90 kd proteins appear as prominent proteins in a variety of different cell types grown in vitro[3]. The effect of growing cells in tissue culture, however, may itself be a stressful situation and thereby result in a slight induction of these proteins as compared to the in vivo tissue.

A comment by Yufu et al. [*Cancer Res.* 49:2405-2408 (1989, pg. 2407)] also has bearing on this point:

Human hsp 70 gene promoter has at least two distinct regulatory domains, a distal domain responsive to heat shock and a proximal domain responsive to simulation by serum[25].

Thus it appears that the presence of the extra gene segment of chromosome 17 in CMT fibroblasts somehow limits the ability of these cells to handle oxidative stress, resulting in the induction of stress proteins.

One or more of the high molecular weight proteins or protein conjugates seen in the study summarized above may be ubiquitin-protein conjugates. This might be the case, for example, with protein SSP 2306, which may correspond to the 55 kDa ubiquitinated conjugate of IMR-90 human diploid lung fibroblasts [Pan et al. *Exp. Gerontol.* 28:39-49 (1993)]. However, no definitive conclusion on this question may be reached based on the data summarized above. The protocol of the inventor's experiment did not include studies involving the use of specific ubiquitin antibodies or ubiquitin-conjugate antibodies and the isoelectric point data tabulated above do not correspond to any of the limited amount of publicly available information which is approximately comparable, such as the HeLa cell ubiquitin conjugate molecular weight and isoelectric point data of Carlson et al. [*J. Cell Biol.* 104:547-555 (1987)].

The unique and completely consistent appearance of four heat shock proteins and twenty-one additional proteins in each of the three chromosome 17 CMT fibroblast strains studied provides the basis for a candidate drug screening procedure which is novel, convenient, suitable for large scale work, cost effective, and requires minimal sacrifice by patients. This is the first rational, empirical system disclosed based on use of living human patient tissue which permits an organized effort aimed at selecting drug candidates appropriate for subsequent use in clinical trials.

Clinical diagnostic tools presently available for characterization of disorders such as Alzheimer's disease and Parkinson's disease have advanced little in the past fifty years. This invention is advantageous in that it permits the examination of a disease state in the absence of end stage and/or postmortem pathology, which tends to obscure early stage pathological events; is based on use of tissue and/or bodily fluid samples which are readily available and, if necessary, repeatedly available; and depends, in part, on use of skin fibroblast cells which grow readily without need of viral transformation, such as that required to maintain lymphocytes in culture. As some of the diseases addressed herein, such as familial Parkinsonism, familial Alzheimer's disease and familial amyotrophic lateral sclerosis, have non-familial counterparts, the present invention may also be of use in developing new diagnostic procedures efficacious in the analysis of these corresponding non-genetic disorders.

The following examples illustrate the present invention without, however, limiting the same thereto.

Example 1

A candidate drug screening protocol may be carried out as follows. Skin punch biopsies are obtained from a patient having a genetic form of a neurodegenerative disease selected from the group hereby limited solely to Charcot-Marie-Tooth disease, familial Alzheimer's disease, familial Parkinson's disease, Huntington's disease, spinal muscular atrophy, Friedreich'a ataxia, giant axon neuropathy, juvenile ceroid-lipofuscinosis, familial motor neuron diseases, juvenile diabetic polyneuropathy and Down's syndrome, including various individual genetic subvarieties thereof, and from an age- and sex-matched control donor. Fibroblast strains are established in culture under standard, generally recognized conditions. For example, each fibroblast strain can be maintained in pH 7.4 RPMI 1640 media supplemented with 10% fetal calf serum and L-glutamine. Fibroblasts can be grown to confluency and then divided 1:3 for each sub-culture. Each cell strain is maintained in culture until confluency of nine T-150 flasks at fifth or sixth passage, then stored in liquid nitrogen at $1 \times 10^6$ cells per vial.

At each sub-culture step, a small sample of cells is aliquoted separately and tested for the expression of stress proteins. For example, the cells may be fixed according to previously recognized methodology [Welch and Suhan *J. Cell Biol.* 103(5):2035-2052 (1986); Milarski et al. *J. Cell Biol.* 108(2):413-423 (1989)] prior to antibody binding. The cells are then labeled with commercially available anti-hsp70 monoclonal antibody alkaline phosphatase conjugate (StressGen Biotechnologies Corp., product number SPA-810AP), followed by incubation in the presence of p-nitrophenyl phosphate colorimetric substrate and standard quantitation by use of commercially available photometric equipment (i.e., photometric tissue culture plate readers).

Each experiment contains the following six sections: (a) patient cells grown under standard culture conditions; (b) patient cells grown under standard culture conditions in the presence of a candidate therapeutic drug; (c) control cells grown under standard culture conditions; (d) control cells grown under standard culture conditions in the presence of a candidate therapeutic drug; (e) control cells grown in presence of a stress protein inducing parameter (i.e., sodium arsenite or ethanol [Pratt and coworkers, 1989]); and (f) control cells grown in the presence of a stress protein inducing factor and a candidate therapeutic drug.

When tested within such an experimental protocol, candidate therapeutic agents which address the specific disease etiology will not prevent chemically induced stress protein expression or and/or other protein modifications indicative of oxidative stress, but will prevent stress protein expression or and/or other protein modifications indicative of oxidative stress in the genetic disease cell strains [section (b)]. Sections (a, (c), (d), and (e) represent various comparative controls which further characterize the drug screening system.

Such an experiment is readily conducted on a single 96-well tissue culture plate. Each of the six sections noted above can occupy 16 wells. So, for example, eight different concentrations of a therapeutic drug candidate can be examined in duplicate. Alternatively, one concentration of a therapeutic drug candidate can be examined at eight different time points. Additionally, various combinations of two or more candidate therapeutic agents may be examined.

Data can be obtained by use of an indicator system for explicitly measuring stress protein expression or and/or other protein modifications indicative of oxidative stress in said cultured fibroblast cells to identify as a drug candidate of possible clinical value, for example, by use of an enzyme linked immunosorbent assay (ELISA) procedure consisting of the following steps. At the end of the tissue culture stage of the experiment, the cells are fixed [Welch and Suhan (1986): Milarski et al. (1989)] prior to antibody binding. Cells are then labeled with commercially available anti-hsp70 monoclonal antibody alkaline phosphatase conjugate (StressGen Biotechnologies Corp., product number SPA-810AP), followed by incubation in the presence of p-nitrophenyl phosphate colorimetric substrate and standard quantitation by use of commercially available photometric equipment (i.e., photometric tissue culture plate readers). Other types of stress protein antibody conjugates can also be used, such as antibody-fluorochrome conjugates (Sigma Chemical Company catalog, 1994, pgs. 1260-1262) and antibody-biotin conjugates (Sigma Chemical Company catalog, 1994, pg. 1262). Variations on the Assay Methodoloay of Example 1

Example 1 describes an ELISA procedure useful for screening of therapeutic drug candidates based, in part, on the use of an antibody-enzyme conjugate. Other antibody-enzyme conjugates may be useful in such ELISA procedures, such as antibody-peroxidase conjugates (Sigma Chemical Company catalog, 1994, pg. 1258) and antibody-urease conjugates (Sigma Chemical Company catalog, 1994, pg. 1259). In various adaptions of the protocol of Example 1, antibodies to hsp70 or hsc70 stress proteins can be conjugated to other indicators such as gold (useful in light microscopy, electron microscopy and immunoblotting procedures; Sigma Chemical Company catalog, 1994, pg. 1262) or ferritin (useful in electron microscopy procedures; Sigma Chemical Company catalog, 1994, pg. 1263). As such, variations on the procedure of Example 1 may be adapted for use in fluorescent immunoassay, immunoblotting, immunohistochemistry, immunocytochemistry and electron microscopy applications.

Additionally, sample analysis subsequent to tissue culture may be carried out by application of various gel electrophoretic procedures well known to those skilled in the art. For example, in the case of fibroblasts obtained from CMT patients having the PMP-22 gene duplication described above, cell samples may be analyzed by one dimensional or two dimensional gel electrophoresis under conditions selected so as to resolve one or more of the high molecular weight disease-specific proteins of 130,000 to 192,000 kDa.

Such assay variations may have useful applications as alternative procedures for screening of candidate therapeutic drugs. The method of this invention can be applied for use with fibroblasts obtained from patients having a genetic neurodegenerative disease selected from the group hereby limited solely to Charcot-Marie-Tooth disease, familial Alzheimer's disease, familial Parkinson's disease, Huntington's disease, spinal muscular atrophy, Friedreich'a ataxia, giant axon neuropathy, juvenile ceroid-lipofuscinosis, familial motor neuron diseases, juvenile diabetic polyneuropathy and Down's syndrome, including various individual genetic subvarieties thereof.

The 1992 report by Piersanti and coworkers documented a increased susceptibility of Alzheimer's disease patient skin fibroblasts to free radical damage. Their evidence of said increased susceptibility was most distinct in fibroblast samples obtained from patients having a familial form of the disease. However, they obtained similar data using fibroblasts obtained from sporadic (i.e., non-genetic) cases of Alzheimer's disease. The Piersant report, together with the type 1a CMT protein mapping data reported herein, provides a basis for understanding that skin fibroblast samples from patients having non-genetic or sporadic forms of other neurodegenerative disorders selected solely from the group consisting of Charcot-Marie-Tooth disease, familial Alzheimer's disease, familial Parkinson's disease, Huntington's disease, spinal muscular atrophy, Friedreich'a ataxia, giant axon neuropathy, juvenile ceroid-lipofuscinosis, familial motor neuron diseases, juvenile diabetic polyneuropathy and Down's syndrome will also provide a practical starting point for use of the fibroblast-based drug screening methodology described herein.

Additionally, protocols as defined above may be applied for use with fibroblasts that have been genetically engineered by use of one or more constructed genetic vector so as to provide a molecular genetic model of a neurodegenerative disease selected solely from the group consisting of Charcot-Marie-Tooth disease, familial Alzheimer's disease, familial Parkinson's disease, Huntington's disease, spinal muscular atrophy, Friedreich'a ataxia, giant axon neuropathy, juvenile ceroid-lipofuscinosis, familial motor neuron diseases, juvenile diabetic polyneuropathy and Down's syndrome.

Hence, in summary, one aspect of the present invention provides a method useful for experimental screening of candidate drug agents based on use of mammalian fibroblasts obtained from a donor having a genetic variety of or a sporadic non-familial variety of a neurodegenerative disorder selected solely from the group noted above, or a fibroblast-based genetically engineered experimental model of a neurodegenerative disorder selected solely from the group noted above; said fibroblasts having been maintained in an in vitro tissue culture environment under circumstances such that they express one or more disease-related proteins which are not translation products of the defective gene responsible for the primary etiological event, if present, and are explicitly stress proteins and/or other protein modifications indicative of oxidative stress; the suppression of said expression of disease-related proteins which are not translation products of the defective gene responsible for the primary etiological event and are explicitly stress proteins and/or other protein modifications indicative of oxidative stress in the presence of a beneficial therapeutic drug agent being a useful indicator of the candidate drug agent's potential clinical value, said suppression being measured by use of indicator systems selected from the group consisting of but not limited to (a) primary antibodies explicitly specific for proteins which are not the product of the defective gene and which are stress proteins and/or one or more other protein modifications indicative of oxidative stress to be used in combination with secondary anti-immunoglobulin conjugates which include biotin, fluorochrome or enzyme indicator functional groups, (b) specific antibody-indicator conjugates specific for proteins which are not the product of the defective gene and which are stress proteins and/or one or more other protein modifications indicative of oxidative stress, said antibody-indicator conjugates including biotin, fluorochrome or enzyme indicator functional groups, (c) radiolabeled antibodies specific for proteins which are not the product of the defective gene and which are explicitly stress proteins and/or one or more other protein modifications indicative of oxidative stress and (d) resolution of proteins which are not the product of the defective gene and which are explicitly stress proteins and/or one or more other protein modifications indicative of oxidative stress according to molecular charge by use of isoelectric focusing gel electrophoresis of said proteins and/or resolution of said proteins according to molecular weight by use of sodium dodecyl sulfate gel electrophoresis, followed by visualization of resolved protein spots on said electrophoresis gel and analysis of the electrophoretic pattern of the resolved cultured fibroblast proteins by visual examination or use of computer-assisted image processing technology, including reference to protein standards of known molecular weight and known isoelectric point.

Likewise, another aspect of the present invention defines a composition which is the analytical system useful for experimental screening of candidate drug agents based on use of mammalian fibroblasts obtained from a donor having a genetic variety of or a sporadic non-familial variety of a neurodegenerative disorder selected solely from the group noted above, or a fibroblast-based genetically engineered experimental model of a neurodegenerative disorder selected solely from the group noted above; said fibroblasts having been maintained in an in vitro tissue culture environment under circumstances such that they express one or more disease-related proteins which are not translation products of the defective gene responsible for the primary etiological event, if present, and are explicitly stress proteins and/or other protein modifications indicative of oxidative stress; the suppression of said expression of disease-related proteins which are not translation products of the defective gene responsible for the primary etiological event and are explicitly stress proteins and/or other protein modifications indicative of oxidative stress in the presence of a beneficial therapeutic drug agent being a useful indicator of the candidate drug agent's potential clinical value, said suppression being measured by use of indicator systems selected from the group consisting of but not limited to (a) primary antibodies specific for proteins which are not the product of the defective gene and which are explicitly stress proteins and/or one or more other protein modifications indicative of oxidative stress to be used in combination with secondary anti-immunoglobulin conjugates which include biotin, fluorochrome or enzyme indicator functional groups, (b) specific antibody-indicator conjugates specific for proteins which are not the product of the defective gene and which are explicitly stress proteins and/or one or more other protein modifications indicative of oxidative stress, said antibody-indicator conjugates including biotin, fluorochrome or enzyme indicator functional groups, (c) radiolabeled antibodies specific for proteins which are not the product of the defective gene and which are explicitly stress proteins and/or one or more other protein modifications indicative of oxidative stress and (d) resolution of proteins which are not the product of the defective gene and which are explicitly stress proteins and/or one or more other protein modifications indicative of oxidative stress according to molecular charge by use of isoelectric focusing gel electrophoresis of said proteins and/or resolution of said proteins according to molecular weight by use of sodium dodecyl sulfate gel electrophoresis, followed by visualization of resolved protein spots on said electrophoresis gel and analysis of the electrophoretic pattern of the resolved cultured fibroblast proteins by visual examination or use of computer-assisted image processing technology, including reference to protein standards of known molecular weight and known isoelectric point.

Methodology Useful in the Characterization of Diagnostic Procedures

The process of reduction to practice for the diagnostic aspects of the present invention may be summarized as follows. As discussed above, a two-dimensional gel electrophoresis study of type 1a CMT fibroblast homogenates revealed the presence of four induced stress proteins and 21 additional proteins not seen in normal fibroblasts. Nine of the 21 additional proteins constituted the highest molecular weight proteins seen in the study, an observation most readily interpreted as evidence of disease-related protein crosslinking. Hence this study revealed evidence of two indications of oxidative stress.

Diagnostic reductions to practice can depend directly on this initial effort. The observations of Piersanti et al. (1992) can be viewed within a broader understanding of the role played by oxidative stress in the etiologies of neurodegenerative diseases [Coyle and Puttfarcken (1993)] and the ability of oxidative stress to stimulate stress protein expression. When taken together with the present inventors protein mapping laboratory findings as summarized above, this information provides a conceptual basis for understanding that one may reasonably expect the occurrence of induced levels of stress proteins, the appearance of disease-related crosslinked proteins and/or other proteins indirectly related to disease etiology in fibroblast samples obtained from patients having any one of several neurodegenerative diseases which are characterized by corresponding pathophysiological phenomena in nerve tissue. It is the new, novel and not previously apparent recognition of such metabolic markers in fibroblast samples, an apparently asymptomatic tissue, which additionally provides the basis for the diagnostic aspects of the present invention.

In fact, a variety of environmental stimuli can induce the expression of stress proteins. So stress proteins are not specific disease markers. Wherever stress protein expression is found in one of these fibroblast disease models, monitoring of it can serve as a useful drug screening protocol, but the observation of such proteins per se does not constitute a specific diagnostic tool.

Further characterization of the other disease-related proteins can be a more useful and practical line of work within a diagnostic context. In the case of type 1a CMT fibroblasts, these cells express 21 additional proteins of this kind. Of the proteins in this class, some can reasonably be expected to be quite disease-specific.

Once a disease-specific protein has been identified by two-dimensional gel electrophoresis, it may be used to develop a monoclonal antibody-producing hybridoma. Each such hybridoma can serve as the basis for a commercially viable, proprietary diagnostic test or for other purposes.

Example 2

In the original type 1a CMT protein mapping experiment described above 30 µg of crude cell homogenate was applied to each gel. Since each gel revealed about 200 protein resolved spots, each spot typically consisted of about 150 ng. Yet each 30 µg protein aliquot was taken from a liquid nitrogen freezer vial which represented the contents of one confluent T-150 tissue culture flask and had a total of about 2 mg protein. So most of the original sample was never used.

The Bio-Rad Laboratories, Inc. "Prep 2-D system" two-dimensional electrophoresis system consists of a "Rotofor" IEF cell for initial sample running and a "Prep Cell" gel tube system for sample running in the second dimension. The Prep 2-D system can accommodate up to 3 mg of protein per run. So three identical gels, representing the contents of three T-150's, can generate about 30 µg of a particular protein. This is the amount of antigen needed to inoculate a mouse as the starting point of a standard hybridoma procedure. At intervals of five days or so, the mouse may be re-inoculated. Then after several weeks the mouse has amplified one or more colonies of spleen cells that produce one or more antigen-specific antibodies. The spleen is then removed, its cells gently suspended and then fused with myeloma cells to produce the desired hybridoma colonies. Each such procedure typically produces perhaps 300 to 500 hybridoma colonies.

After giving the hybridoma colonies about two weeks to establish themselves, their culture media is screened for the presence of antibodies uniquely specific for the original antigen. An appropriate screening assay procedure can be summarized as follows, using 96-well tissue culture plates and a standard ELISA assay. The wells of each screening plate can be prepared by adding a dilute solution of the antigen, incubating overnight at 4° C., removing the antigen solution (reserved for subsequent re-use), rinsing with a bovine serum albumin (BSA) non-specific blocking solution, then removing the BSA stock solution. A drop of used media from each hybridoma colony well is then added to an ELISA assay well, followed by the remainder of the colorimetric procedure. Those hybridoma colonies found to be producing antigen-specific antibody are then cultured further. Such antibody-producing hybridoma colonies can then be further characterized as to the degree of their disease specificity and refined into practical ELISA-based or ELISA-related diagnostic protocols using methodology well known to those skilled in the art.

Methodological Variations on the Procedure of Example 2

A variation on this procedure which can conserve the supply of gel purified antigens can be defined as follows. Sets of two 96-well tissue culture plates are used together for standard ELISA assays. On ELISA screening plate one, a fresh crude homogenate of CMT 1a [or other disease] fibroblast extract is initially used to coat the wells. On ELISA screening plate two, a fresh crude homogenate of normal fibroblast extract is initially used to coat the wells. Drops of used hybridoma media are then applied into the corresponding wells of each plate. The ELISA data from such plate sets are then compared to identify hybridoma colonies which are positive on the CMT 1a ELISA plate but negative on the normal ELISA plate. Such CMT 1a extract specific colonies can then be screened for antibody binding activity using ELISA assays set up with gel-isolated antigens.

The protocol of Example 2 is based on use of the conventional hybridoma procedure, which involves initial in vivo priming of mouse spleen cells followed by fusion to a line of transformed mouse cells, so as to produce immortalized antibody-producing cells. However, alternative laboratory procedures exist which are done entirely in tissue culture and require far less antigenic material. One such procedure is that of Sheng et al. [*Immunology Letters* 16(1):75-81 (1987)].

Hence, use of the methodology summarized above can permit the isolation of hybridoma colonies capable of producing disease-specific monoclonal antibodies. Such antibodies can be used as the basis for a diagnostic test, in tissue screening histologic studies or to possibly identify the presence of sub-clinical amounts of disease-specific anti-gen(s) in patient blood or urine samples obtained from patients having any one of the closed group of neurodegenerative diseases addressed herein. The identification of one or more such disease-specific antigens in patient blood or urine samples can, in turn, provide the basis for simple, photometric, inexpensive clinical or home-use diagnostic assays capable of providing on-going physiological data. Within the context of the present invention, photometric applications shall include direct colorimetric (that is, visual) observation. The histologic applications of such antibody compositions are well known to those skilled in the art, for example, use of the immunocytochemical staining procedure of Lowe et al. [*Neuropath. Appl. Neurobiol.* 15:45-53 (1989), pg. 47], or the two immunocytochemical procedures of Murti et al. [*Proc. Nat. Acad. Sci.* (USA) 85:3019-3023 (1988), pg. 3020]. Likewise, immunoblotting procedures which may employ such antibody compositions are well known [Murti et al. (1988), pg. 3020].

In a further variation on this methodological concept, the possibility that patients having any one of the closed group of neurodegenerative diseases addressed herein may be making sub-clinical amounts of their own disease-specific antibodies (auto-antibodies), which may have escaped previous relatively simplistic attempts to characterize possible patient auto-antibody status, can be considered. Antibody fractions can be isolated from patient blood samples or urine samples and then screened for binding activity to individual disease-specific fibro-blast protein spots isolated by gel electrophoresis. For example, an isolated blood antibody fraction can be labeled by tritium-exchange, then applied to a two-dimensional electrophoresis gel to check for binding to disease-specific protein spots. This procedure, like that summarized in the preceding paragraph, can permit the identification of particular pairs of disease-specific antibodies and antigens. In this case, a sub-clinical level of a disease-specific antibody generated by the patient can be used as an in vivo metabolic marker. Such an antibody metabolic marker, like a possible patient-derived blood or urine antigenic marker as described above, can be used as the basis for a practical diagnostic test based on adapted use of prior art ELISA technology to monitor patient status and response to treatment on an on-going basis or can be used as the basis of a histologic test.

Hence, another aspect of this invention provides a method for the definition of new and novel diagnostic procedures based on use of previously recognized hybridoma technology so as to produce engineered hybridoma cell lines capable of producing antibodies which are specific for epitopes on fibroblast-derived disease-related crosslinked proteins and/or other proteins indirectly related to disease etiology in fibroblast samples obtained from patients having any one of the closed group of neurodegenerative diseases addressed herein, any said antibody-producing hybridoma being useful as (1) a practical tool in the development of an ELISA-based or ELISA-related diagnostic or histologic protocol or (2) a practical tool to monitor the presence of sub-clinical amounts of a disease-specific antigen in patient blood or urine samples.

Additionally, another aspect of this invention provides a method for the definition of new and novel diagnostic procedures based on use of previously recognized hybridoma technology so as to produce engineered hybridoma cell lines capable of producing antibodies which are specific for epitopes on fibroblast-derived disease-related crosslinked proteins and/or other proteins indirectly related to disease etiology in fibroblast samples obtained from patients having any one of the closed group of neurodegenerative diseases addressed herein, any one said antibody being useful as (1) a practical tool in the development of an ELISA-based or ELISA-related diagnostic or histologic protocol or (2) a practical tool to monitor the presence of sub-clinical amounts of a disease-specific antigen in patient blood or urine samples.

Another aspect of this invention provides a method for the definition of new and novel diagnostic procedures based on identification of a disease-related antibody present in patient blood, urine or tissue samples obtained from patients having any one of the closed group of neurodegenerative diseases addressed herein, said antibody characterized by its specific ability to bind to a fibroblast-derived disease-related protein metabolic marker.

Additionally, another aspect of this invention defines at least one new and novel hybridoma cell line composition, each of said at least one engineered hybridoma cell line being capable of producing antibodies which are specific for an epitope on a fibroblast-derived disease-related crosslinked protein and/or other protein indirectly related to disease etiology in fibroblast samples obtained from patients having any one of the closed group of neurodegenerative diseases addressed herein, any said antibody-producing hybridoma being useful as (1) a practical tool in the development of an ELISA-based or ELISA-related diagnostic or histologic protocol or (2) a practical tool to monitor the presence of sub-clinical amounts of a disease-specific antigen in patient blood or urine samples.

Additionally, another aspect of this invention defines at least one new and novel hybridoma-derived antibody composition, each of said at least one antibody being capable of specific binding to an epitope on a fibroblast-derived disease-related crosslinked protein and/or other protein indirectly related to disease etiology in fibroblast samples obtained from patients having any one of the closed group of neurodegenerative diseases addressed herein, any one said antibody being useful as (1) a practical tool in the development of an ELISA-based or ELISA-related diagnostic or histologic protocol or (2) a practical tool to monitor the presence of sub-clinical amounts of a disease-specific antigen in patient blood or urine samples.

Still another aspect of this invention defines at least one patient-derived disease-related antibody obtained from blood, urine or body tissue samples obtained from patients having any one of the closed group of neurodegenerative diseases addressed herein useful for the definition of new and novel diagnostic procedures, each said antibody characterized by its specific ability to bind to a fibroblast-derived disease-related protein metabolic marker.

Without further elaboration the foregoing will so fully illustrate this invention so that others may, by applying current or future knowledge, adapt the same for use under various conditions of service.

I claim:

1. A method for determining if one or more candidate compounds is a potential therapeutic for a neurodegenerative disease, comprising:
   (a) growing fibroblasts from a human donor having the disease,
   (b) contacting the fibroblasts with one or more candidate compounds, and
   (c) measuring the amount of a protein, selected from the group consisting of:
   a protein with apparent molecular weight of 89,300 Daltons and an apparent pI of 4.53
   a protein with apparent molecular weight of 33,100 Daltons and an apparent pI of 4.95
   a protein with apparent molecular weight of 55,100 Daltons and an apparent pI of 5.03
   a protein with apparent molecular weight of 94,200 Daltons and an apparent pI of 5.10 a protein with apparent molecular weight of 130,700 Daltons and an apparent pI of 4.92
a protein with apparent molecular weight of 130,400 Daltons and an apparent pI of 4.97
a protein with apparent molecular weight of 149,000 Daltons and an apparent pI of 4.97
a protein with apparent molecular weight of 149,000 Daltons and an apparent pI of 5.01
a protein with apparent molecular weight of 150,600 Daltons and an apparent pI of 5.11
a protein with apparent molecular weight of 53,000 Daltons and an apparent pI of 5.35
a protein with apparent molecular weight of 145,400 Daltons and an apparent pI of 5.37
a protein with apparent molecular weight of 37,000 Daltons and an apparent pI of 5.71
a protein with apparent molecular weight of 47,600 Daltons and an apparent pI of 5.46
a protein with apparent molecular weight of 63,700 Daltons and an apparent pI of 5.42
a protein with apparent molecular weight of 71,400 Daltons and an apparent pI of 5.57
a protein with apparent molecular weight of 73,400 Daltons and an apparent pI of 5.48
a protein with apparent molecular weight of 67,900 Daltons and an apparent pI of 5.92
a protein with apparent molecular weight of 67,700 Daltons and an apparent pI of 5.84
a protein with apparent molecular weight of 109,500 Daltons and an apparent pI of 5.77
a protein with apparent molecular weight of 29,000 Daltons and an apparent pI of 6.42
a protein with apparent molecular weight of 46,300 Daltons and an apparent pI of 6.48
a protein with apparent molecular weight of 80,300 Daltons and an apparent pI of 6.30
a protein with apparent molecular weight of 138,200 Daltons and an apparent pI of 6.31
a protein with apparent molecular weight of 159,500 Daltons and an apparent pI of 6.25
a protein with apparent molecular weight of 192,800 Daltons and an apparent pI of 6.26
in the fibroblasts that have been contacted with the candidate compound(s),
wherein a decrease in the amount of the protein measured in step (c) as compared to the amount of the protein present in control fibroblasts indicates that the one or more compounds is a potential therapeutic for the disease, and wherein the neurodegenerative disease is Charcot-Marie-Tooth disease.

2. The method of claim 1, wherein the step of measuring comprises an enzyme linked immunosorbent assay, detection of radiolabeled antibodies, an immunhistochemical procedure, a one- or two-dimensional gel electrophoresis procedure followed by protein staining and optionally followed by computer analysis of the stained gel, an immunoblotting procedure, an immunocytochemical procedure, or an electron microscopy procedure.

3. The method of claim 1, wherein the control fibroblasts are fibroblasts from the same human donor having a genetic variety of a neurodegenerative disease grown in the absence of the one or more candidate compounds.

4. The method of claim 3, further comprising control fibroblasts obtained from a genetically normal human donor grown in the presence of the one or more candidate agents.

5. The method of claim 3, further comprising control fibroblasts obtained from a genetically normal human donor grown in the absence of the one or more candidate agents.

6. The method of claim 1, further comprising control fibroblasts obtained from a genetically normal human donor grown in the presence of a stress protein-inducing parameter.

7. The method of claim 6, wherein the control fibroblasts obtained from a genetically normal donor are grown in the presence of a stress protein-inducing parameter and the one or more candidate compounds.

8. The method of claim 6, wherein the stress protein-inducing parameter is a chemical selected from the group consisting of toxic metals, alcohols, metabolic poisons and protein denaturants.

9. The method of claim 6, wherein the stress protein-inducing parameter is selected from the group consisting of exposure to elevated temperatures and exposure to ischemia.

10. The method of claim 1, wherein the fibroblasts are obtained from a skin punch biopsy.

11. A method for determining if one or more candidate compounds is a potential therapeutic for a neurodegenerative disease, comprising:
(a) growing genetically engineered fibroblasts that express a protein that causes the neurodegenerative disease
(b) contacting the fibroblasts with one or more candidate compounds, and
(c) measuring the amount of a protein, selected from the group consisting of:
a protein with apparent molecular weight of 89,300 Daltons and an apparent pI of 4.53
a protein with apparent molecular weight of 33,100 Daltons and an apparent pI of 4.95
a protein with apparent molecular weight of 55,100 Daltons and an apparent pI of 5.03
a protein with apparent molecular weight of 94,200 Daltons and an apparent pI of 5.10
a protein with apparent molecular weight of 130,700 Daltons and an apparent pI of 4.92
a protein with apparent molecular weight of 130,400 Daltons and an apparent pI of 4.97
a protein with apparent molecular weight of 149,000 Daltons and an apparent pI of 4.97
a protein with apparent molecular weight of 149,000 Daltons and an apparent pI of 5.01
a protein with apparent molecular weight of 150,600 Daltons and an apparent pI of 5.11
a protein with apparent molecular weight of 53,000 Daltons and an apparent pI of 5.35
a protein with apparent molecular weight of 145,400 Daltons and an apparent pI of 5.37
a protein with apparent molecular weight of 37,000 Daltons and an apparent pI of 5.71
a protein with apparent molecular weight of 47,600 Daltons and an apparent pI of 5.46
a protein with apparent molecular weight of 63,700 Daltons and an apparent pI of 5.42
a protein with apparent molecular weight of 71,400 Daltons and an apparent pI of 5.57
a protein with apparent molecular weight of 73,400 Daltons and an apparent pI of 5.48
a protein with apparent molecular weight of 67,900 Daltons and an apparent pI of 5.92
a protein with apparent molecular weight of 67,700 Daltons and an apparent pI of 5.84
a protein with apparent molecular weight of 109,500 Daltons and an apparent pI of 5.77 a protein with apparent molecular weight of 29,000 Daltons and an apparent pI of 6.42
a protein with apparent molecular weight of 46,300 Daltons and an apparent pI of 6.48
a protein with apparent molecular weight of 80,300 Daltons and an apparent pI of 6.30
a protein with apparent molecular weight of 138,200 Daltons and an apparent pI of 6.31
a protein with apparent molecular weight of 159,500 Daltons and an apparent pI of 6.25
a protein with apparent molecular weight of 192,800 Daltons and an apparent pI of 6.26
in the fibroblasts that have been contacted with the candidate compound(s),
wherein a decrease in the amount of the protein measured in step (c) as compared to the amount of the protein present in control fibroblasts indicates that the one or more compounds is a potential therapeutic for the disease, and wherein the neurodegenerative disease is Charcot-Marie-Tooth disease.

12. The method of claim 11, wherein the step of measuring comprises an enzyme linked immunosorbent assay, detection of radiolabeled antibodies, an immunhistochemical procedure, a one- or two-dimensional gel electrophoresis procedure followed by protein staining and optionally followed by computer analysis of the stained gel, an immunoblotting procedure, an immunocytochemical procedure, or an electron microscopy procedure.

13. The method of claim 11, wherein control fibroblasts are the same genetically engineered fibroblast experimental model of a human neurodegenerative disease grown in the absence of the one or more candidate agents.

14. The method of claim 13, further comprising control fibroblasts possessing analogous genetic material obtained from a genetically normal human donor grown in the presence of the one or more candidate agents.

15. The method of claim 13, further comprising control fibroblasts possessing analogous genetic material obtained from a genetically normal human donor grown in the absence of the one or more candidate agents.

16. The method of claim 11, further comprising control fibroblasts possessing analogous genetic material obtained from a genetically normal human donor grown in the presence of a stress protein-inducing parameter.

17. The method of claim 16, wherein the control fibroblasts are grown in the presence of a stress protein-inducing parameter and the one or more candidate compounds.

18. The method of claim 16, wherein the stress protein-inducing parameter is a chemical selected from the group consisting of toxic metals, alcohols, metabolic poisons and protein denaturants.

19. The method of claim 16, wherein the stress protein-inducing parameter is selected from the group consisting of exposure to elevated temperatures and exposure to ischemia.

* * * * *